United States Patent
Dowlatkhah et al.

(10) Patent No.: US 10,735,487 B2
(45) Date of Patent: *Aug. 4, 2020

(54) SEGREGATION OF ELECTRONIC PERSONAL HEALTH INFORMATION

(71) Applicants: AT&T Intellectual Property I, L.P., Atlanta, GA (US); AT&T Mobility II LLC, Atlanta, GA (US)

(72) Inventors: Sangar Dowlatkhah, Johns Creek, GA (US); Erie Lai Har Lau, Bellevue, WA (US)

(73) Assignees: AT&T MOBILITY II LLC, Atlanta, GA (US); AT&T INTELLECTUAL PROPERTY I, L.P., Atlanta, GA (US)

(*) Notice: Subject to any disclaimer, the term of this patent is extended or adjusted under 35 U.S.C. 154(b) by 76 days.

This patent is subject to a terminal disclaimer.

(21) Appl. No.: 16/174,604

(22) Filed: Oct. 30, 2018

(65) Prior Publication Data

US 2019/0068675 A1 Feb. 28, 2019

Related U.S. Application Data

(63) Continuation of application No. 14/821,425, filed on Aug. 7, 2015, now Pat. No. 10,171,537.

(51) Int. Cl.
| | |
|---|---|
| *H04L 29/06* | (2006.01) |
| *H04L 29/08* | (2006.01) |
| *H04W 12/02* | (2009.01) |
| *G16H 10/60* | (2018.01) |

(52) U.S. Cl.
CPC ........ *H04L 65/602* (2013.01); *G16H 10/60* (2018.01); *H04L 63/0428* (2013.01); *H04L 65/80* (2013.01); *H04L 67/2804* (2013.01); *H04L 67/2876* (2013.01); *H04W 12/02* (2013.01)

(58) Field of Classification Search
CPC ... H04L 65/602; H04L 65/80; H04L 63/0428; H04L 67/2804; H04L 67/2876; H04W 12/02; G16H 10/60
See application file for complete search history.

(56) References Cited

U.S. PATENT DOCUMENTS

| | | |
|---|---|---|
| 6,138,156 A | 10/2000 | Fletcher et al. |
| 6,931,446 B1 | 8/2005 | Cox et al. |
| 7,581,030 B2 | 8/2009 | Dowling |
| 7,890,576 B2 | 2/2011 | Button et al. |
| 8,046,462 B2 | 10/2011 | Trappeniers et al. |

(Continued)

OTHER PUBLICATIONS

Non-Final Office Action received for U.S. Appl. No. 14/821,425 dated Mar. 31, 2017, 18 pages.

(Continued)

*Primary Examiner* — Blake J Rubin
(74) *Attorney, Agent, or Firm* — Amin, Turocy & Watson, LLP

(57) ABSTRACT

A dynamic secure mobile network is provided to enable the transfer and storage of private data. The dynamic secure mobile network can provide secured communication channels that segregates different types of data and allows for protected data streams to be sent via different secured channels than non-protected data. The enhanced wireless mobile network can support consistent compliancy/privacy and security policies across all networks.

20 Claims, 10 Drawing Sheets

(56) References Cited

U.S. PATENT DOCUMENTS

| | | | |
|---|---|---|---|
| 8,316,237 B1* | 11/2012 | Felsher | H04L 9/0825 380/282 |
| 8,360,975 B1 | 1/2013 | Schwieterman et al. | |
| 8,381,081 B1 | 2/2013 | Subbiah et al. | |
| 8,483,191 B2 | 7/2013 | Erdman et al. | |
| 8,750,123 B1 | 6/2014 | Alisawi | |
| 8,868,661 B2 | 10/2014 | Asawa et al. | |
| 8,984,282 B1 | 3/2015 | Kragh | |
| 9,065,936 B2 | 6/2015 | Goldner et al. | |
| 9,092,643 B2* | 7/2015 | Keoh | H04L 63/0876 |
| 10,395,042 B2* | 8/2019 | Agarwal | H04L 63/10 |
| 10,530,580 B1* | 1/2020 | Walker | H04L 9/3231 |
| 2001/0049790 A1 | 12/2001 | Faccin et al. | |
| 2003/0041048 A1 | 2/2003 | Balasuriya | |
| 2003/0105827 A1 | 6/2003 | Tan et al. | |
| 2003/0191663 A1 | 10/2003 | Sameh | |
| 2004/0203648 A1 | 10/2004 | Wong | |
| 2005/0050017 A1 | 3/2005 | Ross et al. | |
| 2005/0223222 A1* | 10/2005 | Graves | H04L 63/0428 713/165 |
| 2006/0031941 A1 | 2/2006 | Xiao et al. | |
| 2006/0041470 A1 | 2/2006 | Filho et al. | |
| 2007/0027715 A1 | 2/2007 | Gropper et al. | |
| 2007/0043594 A1 | 2/2007 | Lavergne | |
| 2007/0055545 A1 | 3/2007 | Maughan et al. | |
| 2007/0061393 A1* | 3/2007 | Moore | G06F 19/325 709/201 |
| 2007/0086475 A1 | 4/2007 | Clemens et al. | |
| 2007/0157022 A1 | 7/2007 | Blom et al. | |
| 2007/0192140 A1 | 8/2007 | Gropper | |
| 2008/0133716 A1 | 6/2008 | Rao et al. | |
| 2008/0293411 A1 | 11/2008 | Hinton et al. | |
| 2009/0259493 A1 | 10/2009 | Venon et al. | |
| 2010/0151841 A1 | 6/2010 | Metcalf et al. | |
| 2010/0262545 A1 | 10/2010 | Herlitz | |
| 2010/0311402 A1 | 12/2010 | Srinivasan et al. | |
| 2010/0311418 A1 | 12/2010 | Shi et al. | |
| 2010/0312852 A1 | 12/2010 | Kamga et al. | |
| 2010/0332258 A1 | 12/2010 | Dahlke et al. | |
| 2011/0021140 A1 | 1/2011 | Binier | |
| 2011/0028135 A1 | 2/2011 | Srinivasan | |
| 2011/0119088 A1 | 5/2011 | Gunn | |
| 2011/0197237 A1 | 8/2011 | Turner | |
| 2011/0225007 A1 | 9/2011 | Theis | |
| 2011/0243553 A1 | 10/2011 | Russell | |
| 2011/0264460 A1 | 10/2011 | Jagemann et al. | |
| 2011/0282688 A1 | 11/2011 | Raggousis | |
| 2012/0084092 A1 | 4/2012 | Kozuch et al. | |
| 2012/0093303 A1 | 4/2012 | Schultz | |
| 2012/0101847 A1 | 4/2012 | Johnson et al. | |
| 2012/0124651 A1* | 5/2012 | Ganesan | G06F 21/31 726/4 |
| 2012/0155387 A1 | 6/2012 | Simmons et al. | |
| 2012/0172089 A1 | 7/2012 | Bae et al. | |
| 2012/0277543 A1 | 11/2012 | Homchowdhury et al. | |
| 2012/0311657 A1 | 12/2012 | Boldyrev et al. | |
| 2012/0314644 A1 | 12/2012 | Lagerman | |
| 2012/0323691 A1 | 12/2012 | McLaughlin et al. | |
| 2013/0018671 A1* | 1/2013 | Hussam | G16H 40/20 705/3 |
| 2013/0035063 A1 | 2/2013 | Fisk et al. | |
| 2013/0090942 A1 | 4/2013 | Robinson et al. | |
| 2013/0122863 A1 | 5/2013 | Chen et al. | |
| 2013/0124523 A1 | 5/2013 | Rogers et al. | |
| 2013/0132109 A1 | 5/2013 | Mruthyunjaya et al. | |
| 2013/0159288 A1 | 6/2013 | Nikankin | |
| 2013/0231948 A1 | 9/2013 | Kim et al. | |
| 2013/0246084 A1* | 9/2013 | Parmanto | G06F 19/3418 705/2 |
| 2013/0262155 A1 | 10/2013 | Hinkamp | |
| 2013/0290439 A1 | 10/2013 | Blom | |
| 2013/0297821 A1 | 11/2013 | Tanenbaum et al. | |
| 2013/0304486 A1 | 11/2013 | Jagemann et al. | |
| 2013/0326579 A1 | 12/2013 | Bhatti et al. | |
| 2013/0329552 A1 | 12/2013 | Carnero Ros et al. | |
| 2013/0346954 A1 | 12/2013 | Tryon et al. | |
| 2014/0004854 A1 | 1/2014 | Veran et al. | |
| 2014/0039912 A1 | 2/2014 | Turinas et al. | |
| 2014/0047526 A1 | 2/2014 | Huang | |
| 2014/0115507 A1 | 4/2014 | Bailey et al. | |
| 2014/0122119 A1 | 5/2014 | Hardy | |
| 2014/0172366 A1 | 6/2014 | Hannebutte | |
| 2014/0180719 A1 | 6/2014 | Bell et al. | |
| 2014/0185521 A1 | 7/2014 | Aksu et al. | |
| 2014/0207686 A1* | 7/2014 | Experton | G16H 40/20 705/51 |
| 2014/0247716 A1 | 9/2014 | Xiao et al. | |
| 2014/0254491 A1 | 9/2014 | Lindholm et al. | |
| 2014/0343989 A1 | 11/2014 | Martini | |
| 2014/0380044 A1 | 12/2014 | Ashley et al. | |
| 2015/0004967 A1 | 1/2015 | Jiang | |
| 2015/0006723 A1 | 1/2015 | Sheth et al. | |
| 2015/0009826 A1 | 1/2015 | Ma et al. | |
| 2015/0026461 A1 | 1/2015 | Devi | |
| 2015/0039341 A1* | 2/2015 | Markman | G16H 10/60 705/3 |
| 2015/0070516 A1 | 3/2015 | Shoemake et al. | |
| 2015/0074409 A1* | 3/2015 | Reid | H04L 63/061 713/171 |
| 2015/0101066 A1 | 4/2015 | Fram | |
| 2015/0147990 A1 | 5/2015 | Kreitzer et al. | |
| 2015/0172993 A1 | 6/2015 | Jiang | |
| 2015/0188843 A1 | 7/2015 | Chauhan et al. | |
| 2015/0213195 A1 | 7/2015 | Blechman | |
| 2015/0245241 A1 | 8/2015 | Posz | |
| 2015/0296368 A1 | 10/2015 | Kaufman et al. | |
| 2015/0302148 A1* | 10/2015 | Fielder | G06F 16/17 713/193 |
| 2015/0309516 A1 | 10/2015 | Williams et al. | |
| 2015/0381571 A1 | 12/2015 | Plasse et al. | |
| 2016/0006571 A1 | 1/2016 | Teittinen et al. | |
| 2016/0029160 A1 | 1/2016 | Theurer et al. | |
| 2016/0034713 A1 | 2/2016 | Ramirez | |
| 2016/0085915 A1* | 3/2016 | Seow | G16H 10/60 705/3 |
| 2016/0088461 A1 | 3/2016 | Jiang | |
| 2016/0099935 A1* | 4/2016 | Luskin | H04L 63/0823 713/175 |
| 2016/0125471 A1 | 5/2016 | Hsu et al. | |
| 2016/0127777 A1 | 5/2016 | Roberts et al. | |
| 2016/0142878 A1 | 5/2016 | Saulnier | |
| 2016/0156770 A1 | 6/2016 | Vendrow | |
| 2016/0170991 A1 | 6/2016 | Birchall | |
| 2016/0180033 A1 | 6/2016 | Rosenberg | |
| 2016/0203123 A1 | 7/2016 | Kozloski et al. | |
| 2016/0210416 A1 | 7/2016 | Whitehurst | |
| 2016/0210427 A1* | 7/2016 | Mynhier | G16H 10/60 |
| 2016/0260002 A1* | 9/2016 | Hill | G06K 7/10722 |
| 2016/0269891 A1 | 9/2016 | Chen et al. | |
| 2016/0275248 A1 | 9/2016 | Kim et al. | |
| 2016/0277368 A1 | 9/2016 | Narayanaswamy et al. | |
| 2016/0285998 A1 | 9/2016 | Hardy | |
| 2016/0295544 A1 | 10/2016 | Jiang et al. | |
| 2016/0314299 A1 | 10/2016 | Almer | |
| 2016/0315902 A1 | 10/2016 | Silva et al. | |
| 2016/0342767 A1 | 11/2016 | Narasimhan et al. | |
| 2017/0118622 A1 | 4/2017 | Jiang | |
| 2017/0134516 A1 | 5/2017 | Gutman et al. | |
| 2017/0243028 A1 | 8/2017 | LaFever et al. | |
| 2019/0113973 A1* | 4/2019 | Coleman | G06N 5/046 |

OTHER PUBLICATIONS

Final Office Action received for U.S. Appl. No. 14/821,425 dated Sep. 7, 2017, 22 pages.

Non-Final Office Action received for U.S. Appl. No. 14/821,425 dated Jan. 8, 2018, 21 pages.

Notice of Allowance received for U.S. Appl. No. 14/821,425 dated Jul. 31, 2018, 47 pages.

Non-Final Office Action received for U.S. Appl. No. 14/827,028 dated Apr. 5, 2017, 50 pages.

(56) References Cited

OTHER PUBLICATIONS

Non-Final Office Action received for U.S. Appl. No. 14/821,450 dated May 31, 2017, 22 pages.
Non-Final Office Action received for U.S. Appl. No. 14/836,550 dated Aug. 24, 2017, 43 pages.
Final Office Action received for U.S. Appl. No. 14/827,028 dated Sep. 1, 2017, 58 pages.
Notice of Allowance received for U.S. Appl. No. 14/821,450 dated Nov. 28, 2017, 26 pages.
Non-Final Office action received for U.S. Appl. No. 14/827,028 dated Mar. 30, 2018, 53 pages.
Non-Final Office Action received for U.S. Appl. No. 14/929,897 dated May 24, 2018, 43 pages.
Non-Final Office Action received for U.S. Appl. No. 15/910,903 dated Aug. 27, 2018, 29 pages.
Final Office Action received for U.S. Appl. No. 14/827,028 dated Oct. 29, 2018, 51 pages.
Final Office Action received for U.S. Appl. No. 14/929,897 dated Nov. 15, 2018, 30 pages.
Notice of Allowance received for U.S. Appl. No. 14/827,028 dated Dec. 11, 2019, 68 pages.
Non-Final Office Action received for U.S. Appl. No. 14/827,028 dated May 30, 2019, 53 pages.
Non-Final Office Action received for U.S. Appl. No. 16/369,895 dated Jul. 22, 2019, 31 pages.
Non-Final Office Action received for U.S. Appl. No. 14/929,897 dated Aug. 8, 2019, 25 pages.
Final Office Action received for U.S. Appl. No. 14/929,897 dated May 1, 2020, 33 pages.

\* cited by examiner

SEGREGATION OF ELECTRONIC PERSONAL HEALTH INFORMATION

RELATED APPLICATION

The subject patent application is a continuation of, and claims priority to, U.S. patent application Ser. No. 14/821,425, filed Aug. 7, 2015, and entitled "SEGREGATION OF ELECTRONIC PERSONAL HEALTH INFORMATION," the entirety of which application is hereby incorporated by reference herein.

TECHNICAL FIELD

The subject disclosure relates to segregation of electronic personal health information in a wireless communication environment.

BACKGROUND

In order to provide more personalized healthcare to more patients, devices can allow patients to send electronic personal health information to doctors and to monitoring databases. Electronic personal health information is federally regulated, however, and there are strict rules for how mobile applications have to enforce security measures and policies rules at the application layers on the mobile side and at the data storage on the server side. Accordingly, devices in use today are custom built and/or designed to be special purpose devices that cannot be used for other purposes.

DETAILED DESCRIPTION

Figure 1:
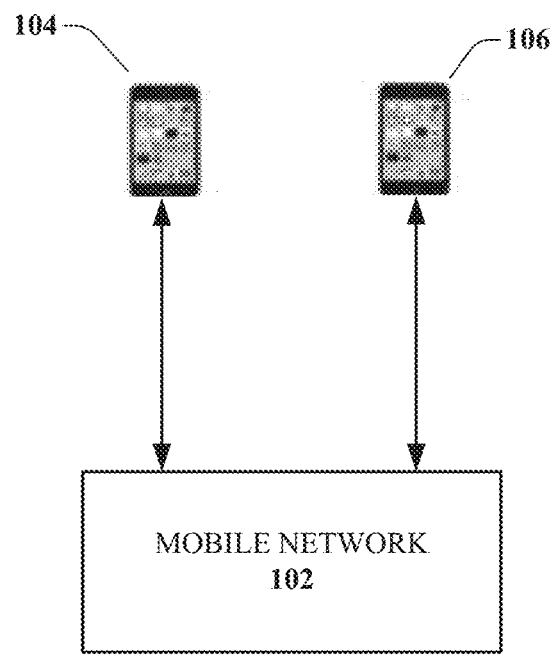
FIG. 1 is an example, non-limiting embodiment of a block diagram showing a dynamic secure mobile network that can support private information in accordance with various aspects described herein.

One or more embodiments are now described with reference to the drawings, wherein like reference numerals are used to refer to like elements throughout. In the following description, for purposes of explanation, numerous specific details are set forth in order to provide a thorough understanding of the various embodiments. It is evident, however, that the various embodiments can be practiced without these specific details (and without applying to any particular networked environment or standard).

In one or more embodiments, a dynamic secure mobile network is provided to enable the transfer and storage of private data. The private data can comprise electronic personal health information (ePHI) that is regulated by the Health Insurance Portability and Accountability Act (HIPAA) that provides for strict rules regarding the handling of ePHI. The dynamic secure mobile network can provide secured communication channels that segregates different types of data and allows for ePHI to be sent via different secured channels than non-ePHI data. The enhanced wireless mobile network can support consistent compliancy/privacy and security policies across all networks (cellular or Wi-Fi) and to provide assurance and authenticity of data integrity and limit misuse of ePHI.

In an embodiment, the dynamic secure mobile network can determine whether data streams in a session contain ePHI, and attach metadata to the streams indicating whether the data streams contain private and/or protected information. The data streams containing ePHI can remain encrypted while the network can perform functions on the data without decrypting the data. The network functions can comprise authentication, providing differentiated quality of experience, granting access bandwidth to the applications generating the ePHI streams (quality of service) depending on the service type (SMS, video streaming, chunk of data, etc). The dynamic secure mobile network can also provide policy driven intelligent persona management to apply different policies per a user profile base.

In an embodiment, the dynamic secure mobile network can provide a trusted common platform for all secured ecosystems. The dynamic secure mobile network can establish secured connection from one device to multipoint ends (supporting HIPAA compliance) in order to enable use of any connected device/application. The dynamic secure mobile network can also provide service independent of operator, access, device and location. By enabling carrier grade authentication through triplets and virtual SIM enabled subsystem, the dynamic secure mobile network can accommodate any device, anywhere in the world.

For these considerations as well as other considerations, in one or more embodiments, a system comprises a processor and a memory that stores executable instructions that, when executed by the processor, facilitate performance of operations, comprising receiving a first data stream from a device. The operations also comprise determining that the first data stream comprises protected information based on an indication of a type of application associated with the first data stream and adding metadata to the first data stream indicating that the first data stream comprises the protected information resulting in a modified first data stream. The operations also comprise segregating the modified first data stream from a second data stream provided by the device, the second data stream not comprising the protected information, based on the metadata of the modified first data stream and transmitting the modified first data stream and the second data stream via a network device of a mobile network.

In another embodiment, a method comprises receiving, by a device comprising a processor, a first data stream from a user equipment. The method also comprises determining, by the device, that the first data stream comprises private information based on a determination of an application on the user equipment associated with the first data stream. The method also comprises generating, by the device, metadata that indicates that the first data stream comprises private information. The method can also comprise attaching the metadata to the first data stream resulting in an updated first data stream and segregating the updated first data stream from a second data stream provided by the user equipment, the second data stream not comprising the private information, based on the metadata of the updated first data stream. The method can also comprise transmitting, by the device, the updated first data stream and the second data stream via a network device of a mobile network.

In another embodiment, a machine-readable storage medium, comprising executable instructions that, when executed by a processor, facilitate performance of operations comprising receiving a data stream from a user equipment. The operations also comprise determining that the data stream comprises private information based on an application on the user equipment associated with the data stream and adding metadata to the data stream that indicates that the data stream comprises private information. The operations further comprise maintaining the data stream separate from another data stream received from the user equipment, the other data stream not comprising the private information, based on the metadata of the data stream and transmitting the data stream and the other data stream via a network device of a network.

Turning now to FIG. 1, illustrated is an example, non-limiting embodiment of a block diagram 100 showing a dynamic secure mobile network that can support private information in accordance with various aspects described herein.

A mobile broadband network 102 generally comprises a radio access network that facilitates communications between the mobile devices 104 and 106 and a core network. In the case of Long Term Evolution ("LTE") networks and other 3rd Generation Partnership Project ("3GPP") compliant networks (e.g., LTE Advanced) and even non-3G-PP systems such as WiMAX and CDMA2000, these networks are the radio access network and an evolved packet core network that can contain a series of components that provide mobile data and control management. The dynamic secure mobile network system disclosed herein can be utilized in network that comprises base station devices (eNodeBs) and WiFi access points and other network access points. In some embodiments, the dynamic secure mobile network system can be operable with user equipment or networked devices that are not directly attached to a mobile network system but rather have wireline networked access. For the sake of simplicity, throughout this application, reference will be made to a mobile network, but the subject matter disclosed herein can be operable in any networked environment.

In an embodiment, mobile network 102 can be in communication with a mobile device or other user equipment 104. In some embodiments, the user equipment 104 can be a mobile device, tablet, laptop, or desktop computer, or any other computing device. An active session that the user equipment 104 has with the mobile network 102 can have one or more data streams depending on which applications are active on the user equipment 104. For instance, each application active on the user equipment can have one or more data streams with the mobile network 102. In an embodiment, the mobile network 102 can transfer one or more of the data streams from the user equipment 104 to user equipment 106. If a data stream contains private information or information that is otherwise protected, the data stream can be segregated from other data streams when being handled by the mobile network 102.

Private and/or protected information can comprise electronic personal health information (ePHI) which refers to any protected health information (PHI) that is regulated (e.g., HIPAA). Private information can also comprise proprietary information, national security information, or other information in which it may be desirable to handle separately from non-private information.

The mobile network 102 can receive one or more streams from the user equipment 104, and determine whether the streams contain protected information. The mobile network 102 can determine whether the streams contain protected information based on an application that is associated with the data streams. For instance, if an application on the user equipment 104 is configured to record health care information about a person or transmit health care information, data streams associated with the application are very likely to contain ePHI, and so the mobile network 102 can segregate those data streams from other data streams coming from the user equipment 104. The mobile network 102 can examine metadata on the streams to determine from which applications the streams originated, or can determine the applications based on the formatting or types of streams.

In an embodiment, mobile network 102 can use other contextual information to determine whether the streams contain protected information. For instance, if the protected information is health care information, mobile network 102 can determine that the user equipment 104 is streaming protected information based on the location (e.g., in an examining room), or time of day (e.g., scheduled checkups), or user profile that is active on user equipment 104. In other embodiments, mobile network 102 can user other contextual information to determine whether the data streams contain protected information.

When mobile network 102 determines that the data stream contains protected information, the mobile network 102, via a metadata broker system (shown in FIG. 6) can attach and/or append metadata to the data streams and the mobile network 102 can transmit the data stream to the user equipment 106 while segregating the data stream from the data streams that contain unprotected information. In an embodiment, the data stream that has protected information can remain encrypted while the mobile network 102 routes and transmits the data stream to the user equipment 106.

Figure 2:
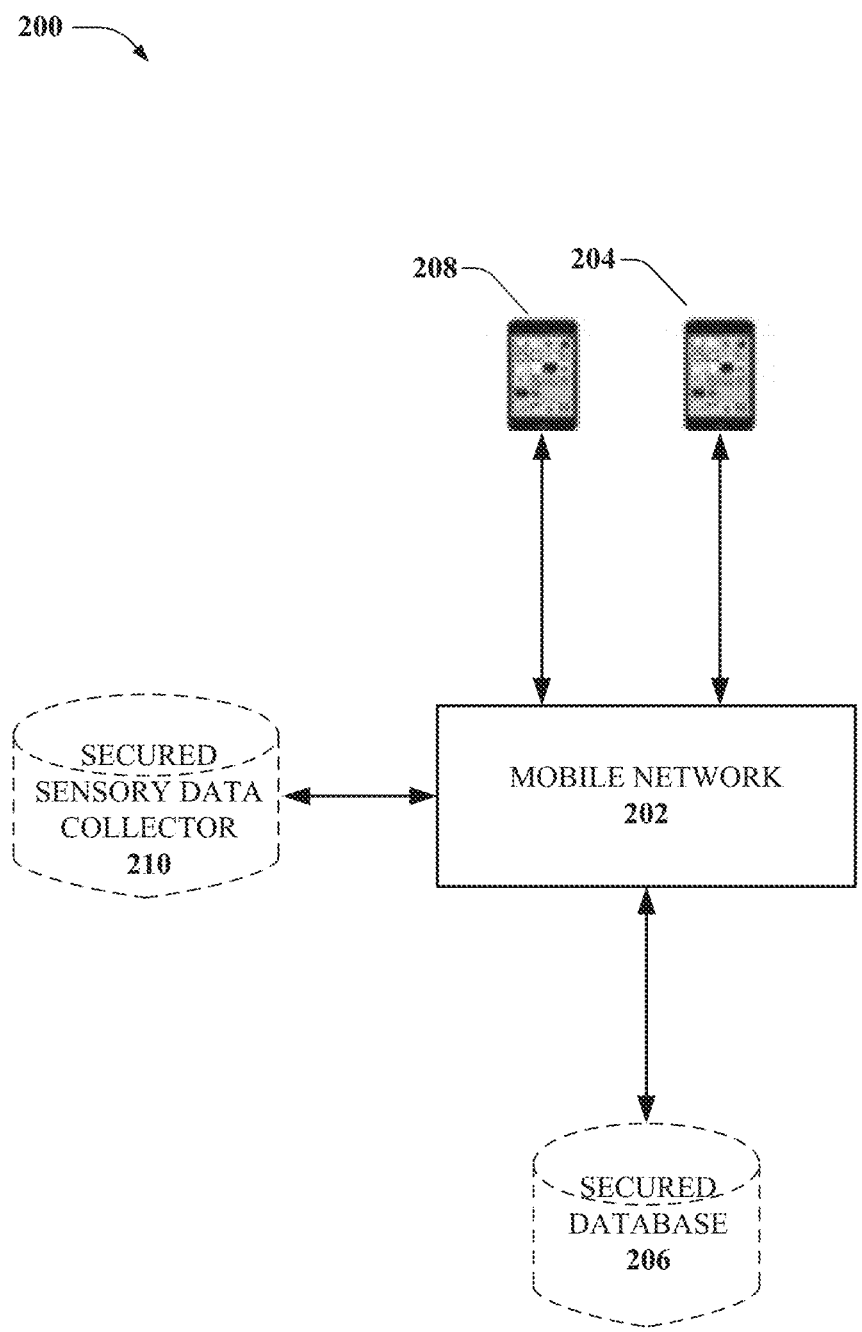
FIG. 2 is an example, non-limiting embodiment of a block diagram showing a dynamic secure mobile network that can support private information in accordance with various aspects described herein.

Turning now to FIG. 2, illustrated is an example, non-limiting embodiment of a block diagram 200 showing a dynamic secure mobile network that can support private information in accordance with various aspects described herein.

Similar to the embodiment shown in FIG. 1, in FIG. 2, the mobile network 202 can identify streams from user equipment 204 that contain protected information, and then segregate those streams from other streams when transmitting the data to a secured database 206. The secured database 206 can receive ePHI relating to multiple patients/individuals from multiple user equipments, and keep the data segregated from each other.

In an embodiment, mobile network 202 can be in communication with a mobile device or other user equipment 204. In some embodiments, the user equipment 204 can be a mobile device, tablet, laptop, or desktop computer, or any other computing device. An active session that the user equipment 204 has with the mobile network 202 can have one or more data streams depending on which applications are active on the user equipment 204. For instance, each application active on the user equipment can have one or more data streams with the mobile network 202. In an embodiment, the mobile network 202 can transfer one or more of the data streams from the user equipment 204 to secured database 206. If a data stream contains private information or information that is otherwise protected, the data stream can be segregated from other data streams when being handled by the mobile network 202.

In an embodiment, a device 208 can be provided to collect sensory data, using one or more sensors (e.g., light, motion, audio, pressure, etc). The sensory data can include sensory data related to biomarkers such as heart rate, blood pressure, etc. The sensory data can be stored in a remote secured sensory data collector 210 communicably coupled to the mobile network 202.

Figure 3:
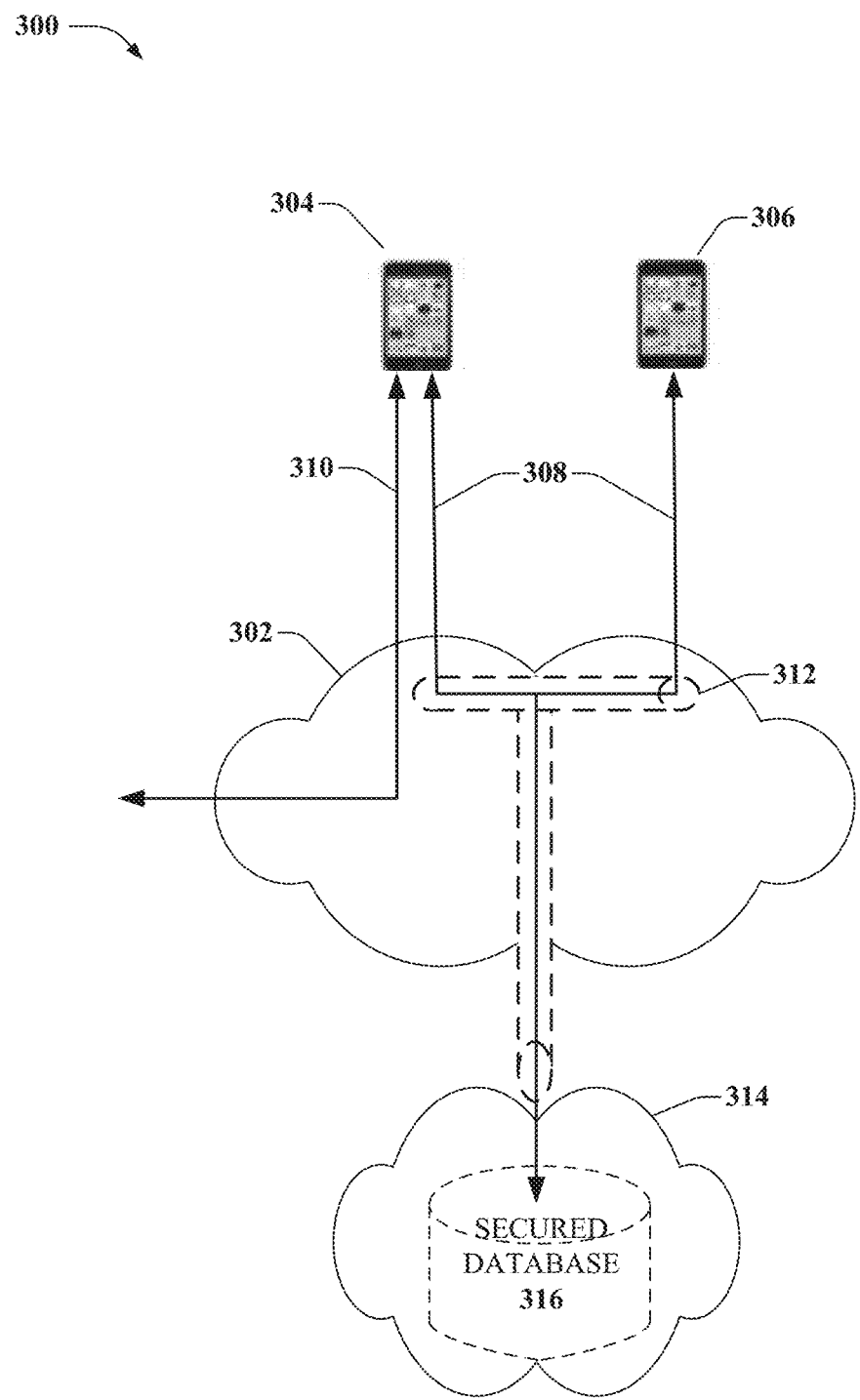
FIG. 3 is an example, non-limiting embodiment of a block diagram showing a dynamic secure mobile network that can support private information in accordance with various aspects described herein.

Turning now to FIG. 3, illustrated is an example, non-limiting embodiment of a block diagram 300 showing a dynamic secure mobile network that can support private information in accordance with various aspects described herein.

In an embodiment, mobile network 302 can be in communication with a mobile device or user equipment 304 and 306. In some embodiments, the user equipment 304 and 306 can be mobile devices, tablets, laptops, or desktop computers, or any other computing devices. An active session that the user equipment 304 has with the mobile network 302 can have one or more data streams (e.g., data streams 308 and 310) depending on which applications are active on the user equipment 304. For instance, each application active on the user equipment can have one or more data streams with the mobile network 302. In an embodiment, the mobile network 302 can transfer data stream 308 from user equipment 304 to user equipment 306 if mobile network 302 determines that data stream 308 contains private or protected information. Mobile network 302 can also transfer the data stream 308 to a secured database 316 in another network 314.

Mobile network 302 can segregate data streams 308 and 310 and keep them segregated within the mobile network 302. The streams can both be received via the same active session, but mobile network 302 can route the protected stream 302 to user equipment 306 via a secure route 312, while transferring the stream 302 elsewhere. In some embodiments, both streams 308 can 310 can be transmitted to the user equipment 306, but remain segregated during transfer.

In an embodiment, mobile network 302 can use other contextual information to determine whether the streams contain protected information. For instance, if the protected information is health care information, mobile network 302 can determine that the user equipment 304 is streaming protected information based on the location (e.g., in an examining room), or time of day (e.g., scheduled checkups), or user profile that is active on user equipment 304.

Mobile network 302, via a metadata broker system, can add metadata to the protected data stream 308 to indicate that the data stream contains protected information. The metadata can allow the mobile network 302 to distinguish the protected data stream from the unprotected data streams (e.g., data stream 310).

The data stream 308 containing ePHI can remain encrypted while being transported from user equipment 304 to user equipment 306 while the network can perform functions on the data without decrypting the data. The network functions can comprise authentication, providing differentiated quality of experience, granting access bandwidth to the applications generating the ePHI streams (quality of service) depending on the service type (SMS, video streaming, chunk of data, etc). The dynamic secure mobile network can also provide policy driven intelligent persona management to apply different policies per a user profile base.

The other network 314 that has the secured database 316 can also comprise other databases that can store ePHI data. In some embodiments, user equipment 306 which may be associated with a doctor or a researcher, can request ePHI data from the secured database 316 or other databases, and mobile network 302 can facilitate the transfer of the ePHI data performing the same segregation and security protocols on the data as data stream 308 received from user equipment 304.

Figure 4:
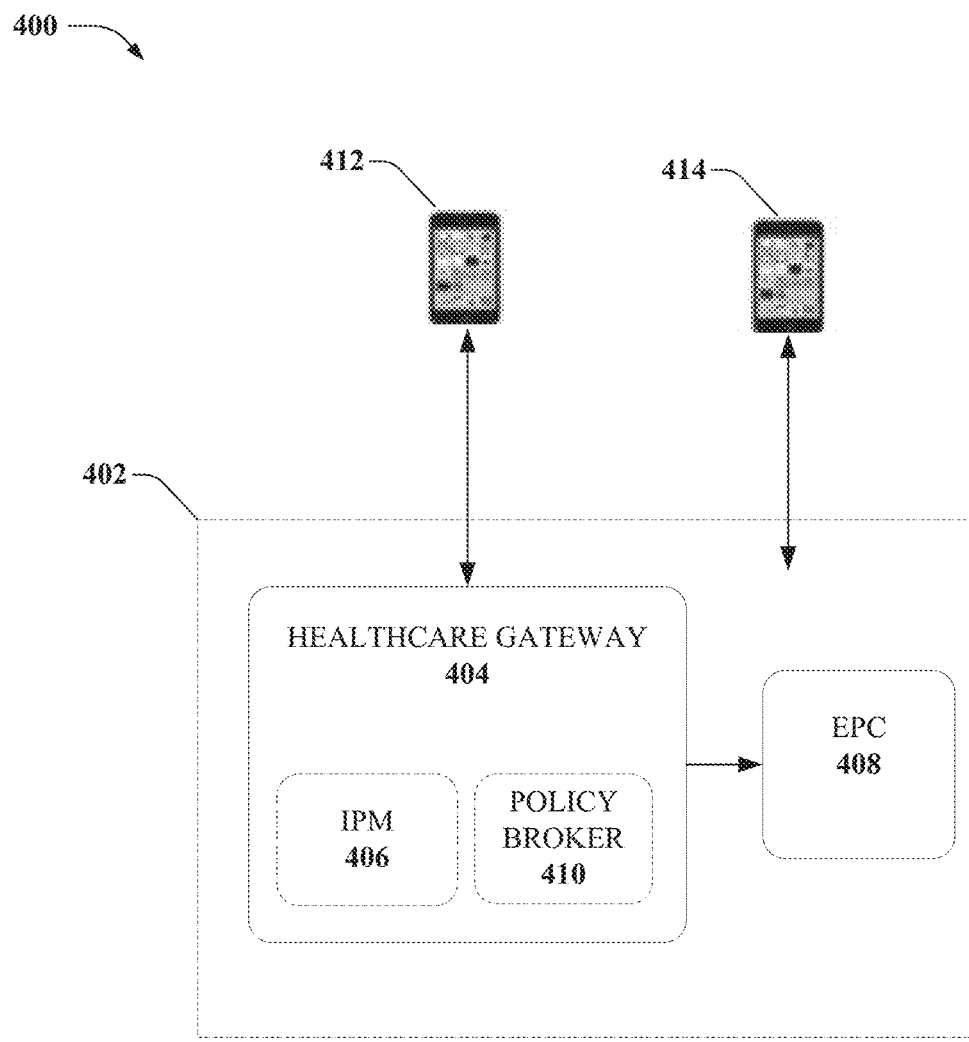
FIG. 4 is an example, non-limiting embodiment of a block diagram showing a HIPAA compliant dynamic secure mobile network in accordance with various aspects described herein.

Turning now to FIG. 4, illustrated is a an example, non-limiting embodiment of a block diagram 400 showing a HIPAA compliant dynamic secure mobile network in accordance with various aspects described herein.

In an embodiment, mobile network 402 can comprise a healthcare gateway 404 that receives one or more data streams from a user equipment 412. The user equipment 412 can be a wireless or wireline computing device that has a data streams that are routed through the healthcare gateway 404 before being routed to the rest of the EPC 408 in the network 402 before being transmitted to user equipment 414.

The healthcare gateway 404 can determine whether the data streams contain protected information, and can use an intelligent persona manager 406 to apply different policies per user profile base. For instance, depending on the user profile logged into the user equipment 412, data streams from a first application may or may not contain ePHI or otherwise protected information. The IPM 406 can also contain information regarding policies directing how protected information is to be handled and segregated. The healthcare gateway 404 can also comprise a metadata broker that can attach or append metadata to the streams so that the EPC 408 can differentiate protected and unprotected streams and treat the protected streams differently than unprotected streams. The policy broker/aggregator 410 can comprise information regarding quality of service and quality experience with the streams, based on the IPM 406 policies and the applications in use on the user equipment 412.

In an embodiment, the mobile network 402 can also send secured data from the mobile network 402 to either mobile device 412 or 414 via a secured channel. The secured data can be sent via the healthcare gateway 404 (or any network gateway such as a serving gateway, packet data gateway, etc) or via an application server on mobile network 402. An example of the secured data that can be sent by the mobile network 402 include push messages containing private or protected information.

Figure 5:
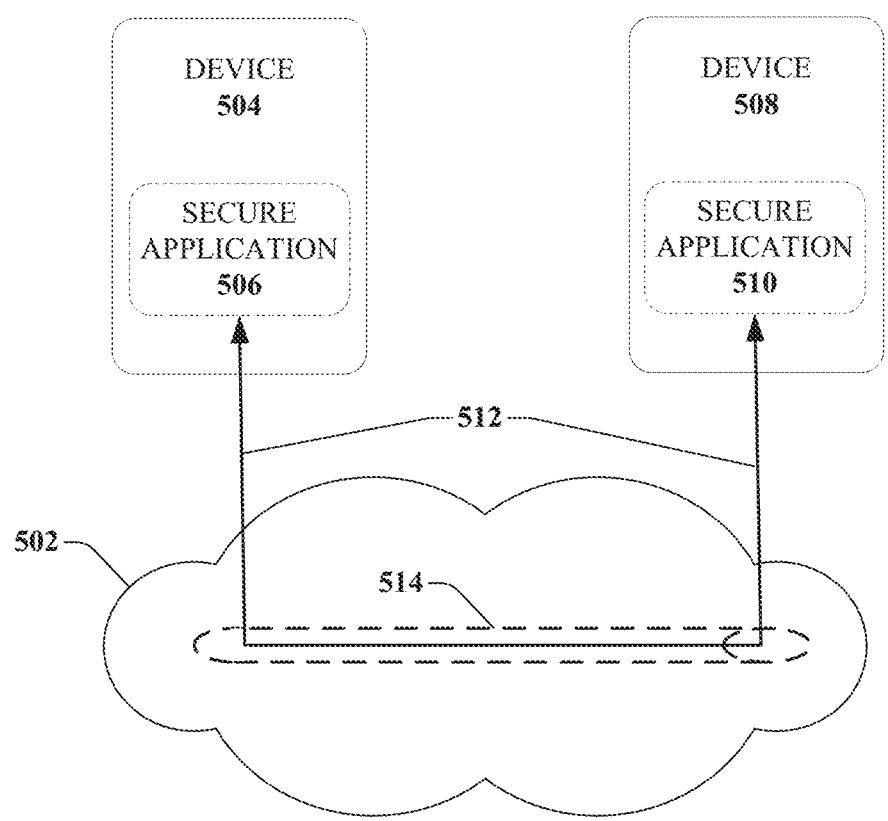
FIG. 5 is an example, non-limiting embodiment of a block diagram showing a dynamic secure mobile network that can support private information in accordance with various aspects described herein.

Turning now to FIG. 5, illustrated is an example, non-limiting embodiment of a block diagram 500 showing a dynamic secure mobile network that can support private information in accordance with various aspects described herein. In an embodiment, the mobile network 502 can enable a real time communication between devices 504 and 508 via secure applications 506 and 510 on devices 504 and 508 respectively.

The mobile network 502 can facilitate setting up a secure connection 514 for a data stream 512 between the devices 504 and 508 based on a secure real-time connection that is negotiated by APIs in the secure applications 506 and 510. In some embodiments, the secure applications 506 and 510 can be browsers or service portals.

Figure 6:
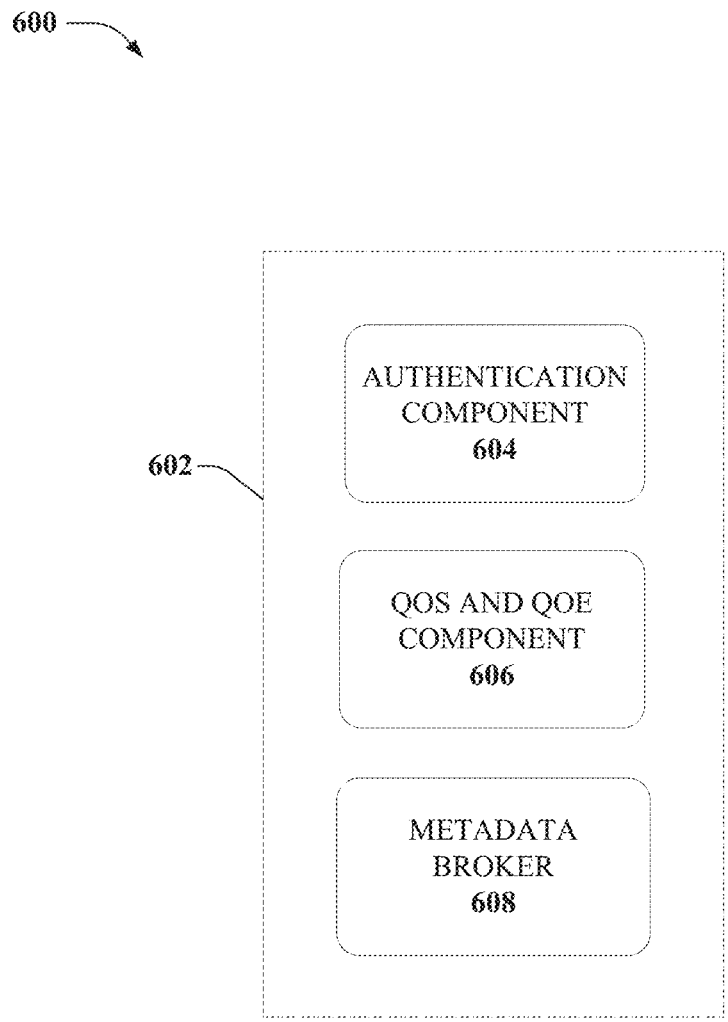
FIG. 6 is an example, non-limiting embodiment of a block diagram showing a healthcare gateway that can support private information in accordance with various aspects described herein.

Turning now to FIG. 6, illustrated is an example, non-limiting embodiment of a block diagram 600 showing a healthcare gateway 602 that can support private information in accordance with various aspects described herein.

An authentication component 604 in the healthcare gateway device can authenticate sessions and/or data streams from user equipment using triplets and virtual SIMs. This can allow the user equipment to be independent of operator, access, device, and location.

The QoS and QoE component 606 can provide quality of service and quality of experience network functionality to the data streams containing protected information. The QoS and QoE component 606 can apply the network functions based on policies in a policy broker/aggregator on the network or in an intelligent persona manager on the healthcare gateway 602.

A metadata broker 608 can examine the data streams from the user equipment and attach metadata to the streams that are determined to contain private and/or protected information. The metadata broker 608 can determine whether the streams contain protected information based on an application that is associated with the data streams. For instance, if an application on the user equipment is configured to record health care information about a person or transmit health care information, data streams associated with the application are very likely to contain ePHI, and so the metadata broker 608 can segregate those data streams from other data streams coming from the user equipment. The metadata broker 608 can examine metadata on the streams to determine from which applications the streams originated, or can determine the applications based on the formatting or types of streams.

The metadata broker 608 can use other contextual information to determine whether the streams contain protected information. For instance, if the protected information is health care information, metadata broker 608 can determine that the user equipment is streaming protected information based on the location (e.g., in an examining room), or time of day (e.g., scheduled checkups), or user profile that is active on user equipment. In other embodiments, metadata broker 608 can user other contextual information to determine whether the data streams contain protected information.

Figure 7:
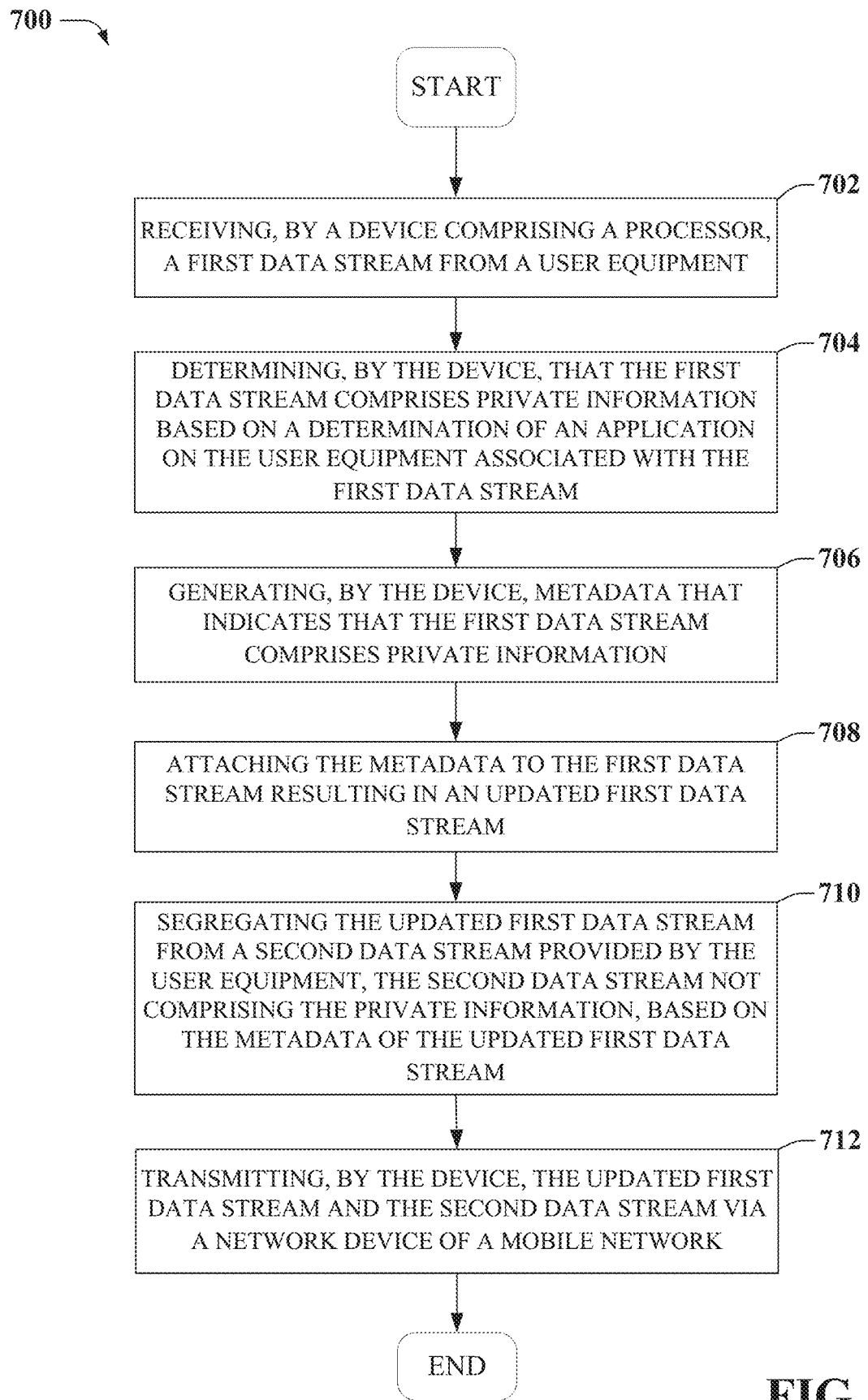
FIG. 7 illustrates a flow diagram of an example, non-limiting embodiment of a method for providing a dynamic secure mobile network as described herein.
Figure 8:
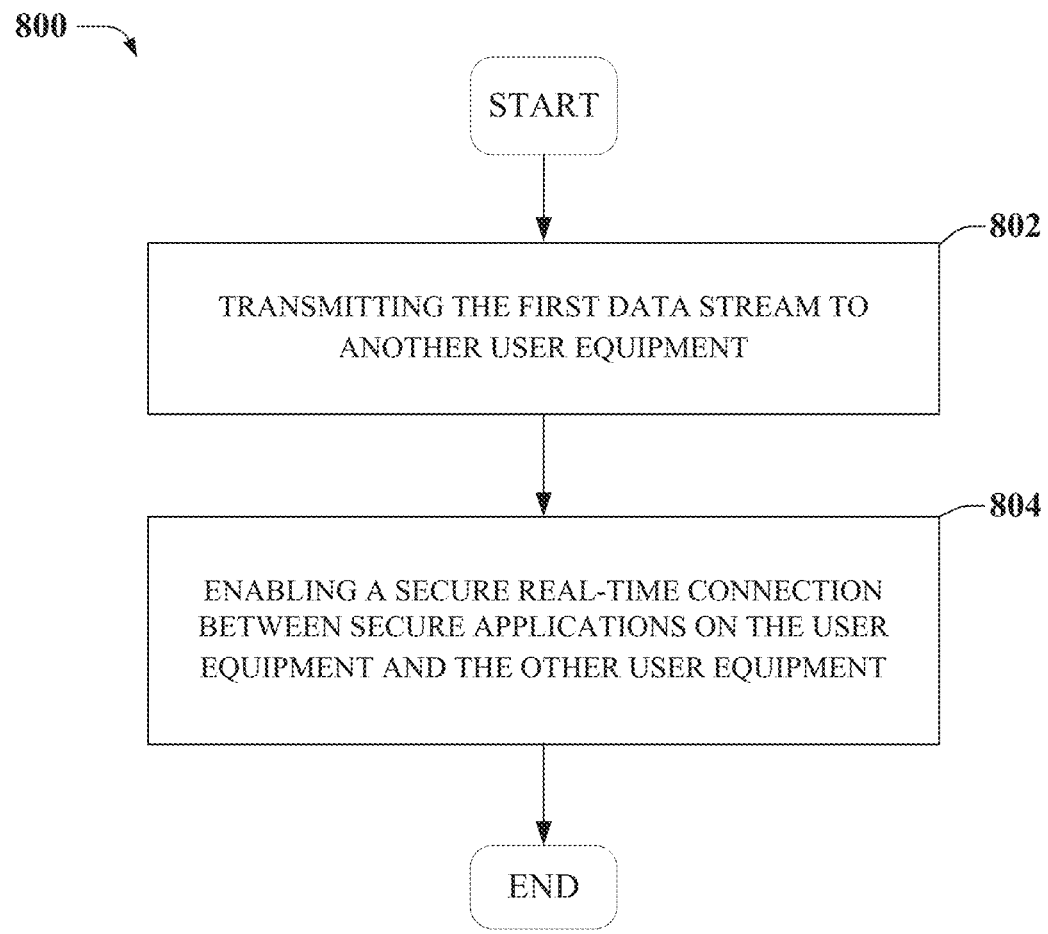
FIG. 8 illustrates a flow diagram of an example, non-limiting embodiment of a method for providing a dynamic secure mobile network as described herein.

FIGS. 7-8 illustrates a process in connection with the aforementioned systems. The processes in FIGS. 7-8 can be implemented for example by the systems in FIGS. 1-6. While for purposes of simplicity of explanation, the methods are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described hereinafter.

FIG. 7 illustrates a flow diagram of an example, non-limiting embodiment of a method 700 for providing a dynamic secure mobile network as described herein.

Method 700 can begin at 702 where the method comprises receiving, by a device comprising a processor, a first data stream from a user equipment.

At method step 704, the method comprises determining, by the device, that the first data stream comprises private information based on a determination of an application on the user equipment associated with the first data stream. At 706, the method comprises generating, by the device, metadata that indicates that the first data stream comprises private information. At 708, the method comprises attaching the metadata to the first data stream resulting in an updated first data stream.

At 710, the method comprises segregating the updated first data stream from a second data stream provided by the user equipment, the second data stream not comprising the private information, based on the metadata of the updated first data stream and at 712, the method comprises transmitting, by the device, the updated first data stream and the second data stream via a network device of a mobile network.

Turning now to FIG. 8, illustrates a flow diagram of an example, non-limiting embodiment of a method 800 for providing a dynamic secure mobile network as described herein.

Method 800 can begin at 802 where the method comprises transmitting the first data stream to another user equipment. At 804 the method comprises enabling a secure real-time connection between secure applications on the user equipment and the other user equipment.

Figure 9:
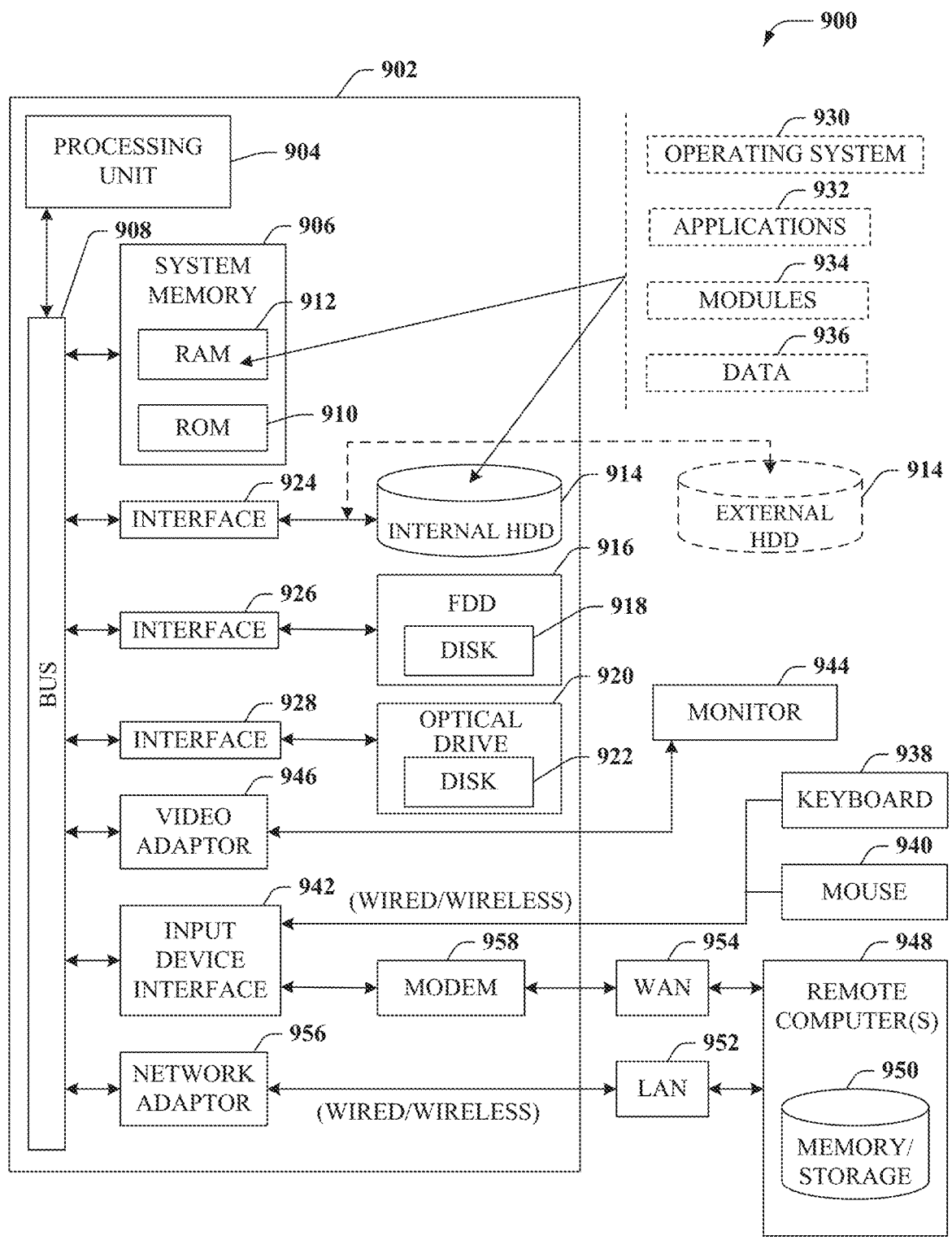
FIG. 9 is a block diagram of an example, non-limiting embodiment of a computing environment in accordance with various aspects described herein.

Referring now to FIG. 9, there is illustrated a block diagram of a computing environment in accordance with various aspects described herein. For example, in some embodiments, the computer can be or be included within the radio repeater system disclosed in any of the previous systems 200, 300, 400, 500, 600, and/or 700.

In order to provide additional context for various embodiments described herein, FIG. 9 and the following discussion are intended to provide a brief, general description of a suitable computing environment 900 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, comprising single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The terms "first," "second," "third," and so forth, as used in the claims, unless otherwise clear by context, is for clarity only and doesn't otherwise indicate or imply any order in time. For instance, "a first determination," "a second determination," and "a third determination," does not indicate or imply that the first determination is to be made before the second determination, or vice versa, etc.

The illustrated embodiments of the embodiments herein can be also practiced in distributed computing environments where certain tasks are performed by remote processing devices that are linked through a communications network.

In a distributed computing environment, program modules can be located in both local and remote memory storage devices.

Computing devices typically comprise a variety of media, which can comprise computer-readable storage media and/or communications media, which two terms are used herein differently from one another as follows. Computer-readable storage media can be any available storage media that can be accessed by the computer and comprises both volatile and nonvolatile media, removable and non-removable media. By way of example, and not limitation, computer-readable storage media can be implemented in connection with any method or technology for storage of information such as computer-readable instructions, program modules, structured data or unstructured data.

Computer-readable storage media can comprise, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage or other magnetic storage devices or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and comprises any information delivery or transport media. The term "modulated data signal" or signals refers to a signal that has one or more of its characteristics set or changed in such a manner as to encode information in one or more signals. By way of example, and not limitation, communication media comprise wired media, such as a wired network or direct-wired connection, and wireless media such as acoustic, RF, infrared and other wireless media.

With reference again to FIG. 9, the example environment 900 for implementing various embodiments of the aspects described herein comprises a computer 902, the computer 902 comprising a processing unit 904, a system memory 906 and a system bus 908. The system bus 908 couples system components comprising, but not limited to, the system memory 906 to the processing unit 904. The processing unit 904 can be any of various commercially available processors. Dual microprocessors and other multi-processor architectures can also be employed as the processing unit 904.

The system bus 908 can be any of several types of bus structure that can further interconnect to a memory bus (with or without a memory controller), a peripheral bus, and a local bus using any of a variety of commercially available bus architectures. The system memory 906 comprises ROM 910 and RAM 912. A basic input/output system (BIOS) can be stored in a non-volatile memory such as ROM, erasable programmable read only memory (EPROM), EEPROM, which BIOS contains the basic routines that help to transfer information between elements within the computer 902, such as during startup. The RAM 912 can also comprise a high-speed RAM such as static RAM for caching data.

The computer 902 further comprises an internal hard disk drive (HDD) 914 (e.g., EIDE, SATA), which internal hard disk drive 914 can also be configured for external use in a suitable chassis (not shown), a magnetic floppy disk drive (FDD) 916, (e.g., to read from or write to a removable diskette 918) and an optical disk drive 920, (e.g., reading a CD-ROM disk 922 or, to read from or write to other high capacity optical media such as the DVD). The hard disk drive 914, magnetic disk drive 916 and optical disk drive 920 can be connected to the system bus 908 by a hard disk drive interface 924, a magnetic disk drive interface 926 and an optical drive interface 928, respectively. The interface 924 for external drive implementations comprises at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 902, the drives and storage media accommodate the storage of any data in a suitable digital format. Although the description of computer-readable storage media above refers to a hard disk drive (HDD), a removable magnetic diskette, and a removable optical media such as a CD or DVD, it should be appreciated by those skilled in the art that other types of storage media which are readable by a computer, such as zip drives, magnetic cassettes, flash memory cards, cartridges, and the like, can also be used in the example operating environment, and further, that any such storage media can contain computer-executable instructions for performing the methods described herein.

A number of program modules can be stored in the drives and RAM 912, comprising an operating system 930, one or more application programs 932, other program modules 934 and program data 936. All or portions of the operating system, applications, modules, and/or data can also be cached in the RAM 912. The systems and methods described herein can be implemented utilizing various commercially available operating systems or combinations of operating systems.

A user can enter commands and information into the computer 902 through one or more wired/wireless input devices, e.g., a keyboard 938 and a pointing device, such as a mouse 940. Other input devices (not shown) can comprise a microphone, an infrared (IR) remote control, a joystick, a game pad, a stylus pen, touch screen or the like. These and other input devices are often connected to the processing unit 904 through an input device interface 942 that can be coupled to the system bus 908, but can be connected by other interfaces, such as a parallel port, an IEEE 1394 serial port, a game port, a universal serial bus (USB) port, an IR interface, etc.

A monitor 944 or other type of display device can be also connected to the system bus 908 via an interface, such as a video adapter 946. In addition to the monitor 944, a computer typically comprises other peripheral output devices (not shown), such as speakers, printers, etc.

The computer 902 can operate in a networked environment using logical connections via wired and/or wireless communications to one or more remote computers, such as a remote computer(s) 948. The remote computer(s) 948 can be a workstation, a server computer, a router, a personal computer, portable computer, microprocessor-based entertainment appliance, a peer device or other common network node, and typically comprises many or all of the elements described relative to the computer 902, although, for purposes of brevity, only a memory/storage device 950 is illustrated. The logical connections depicted comprise wired/wireless connectivity to a local area network (LAN) 952 and/or larger networks, e.g., a wide area network (WAN) 954. Such LAN and WAN networking environments are commonplace in offices and companies, and facilitate enterprise-wide computer networks, such as intranets, all of which can connect to a global communications network, e.g., the Internet.

When used in a LAN networking environment, the computer 902 can be connected to the local network 952 through a wired and/or wireless communication network interface or adapter 956. The adapter 956 can facilitate wired or wireless communication to the LAN 952, which can also comprise a wireless AP disposed thereon for communicating with the wireless adapter 956.

When used in a WAN networking environment, the computer 902 can comprise a modem 958 or can be connected to a communications server on the WAN 954 or has other means for establishing communications over the WAN 954, such as by way of the Internet. The modem 958, which can be internal or external and a wired or wireless device, can be connected to the system bus 908 via the input device interface 942. In a networked environment, program modules depicted relative to the computer 902 or portions thereof, can be stored in the remote memory/storage device 950. It will be appreciated that the network connections shown are example and other means of establishing a communications link between the computers can be used.

The computer 902 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This can comprise Wireless Fidelity (Wi-Fi) and BLUETOOTH® wireless technologies. Thus, the communication can be a predefined structure as with a conventional network or simply an ad hoc communication between at least two devices.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, n, ac, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 11 Mbps (802.11a) or 54 Mbps (802.11b) data rate, for example or with products that contain both bands (dual band), so the networks can provide real-world performance similar to the basic 10BaseT wired Ethernet networks used in many offices.

In an embodiment of the subject application, the computer 1002 can provide the environment and/or setting in which one or more of the dynamic secure mobile network systems disclosed in FIGS. 1-6 can be operated from.

Figure 10:
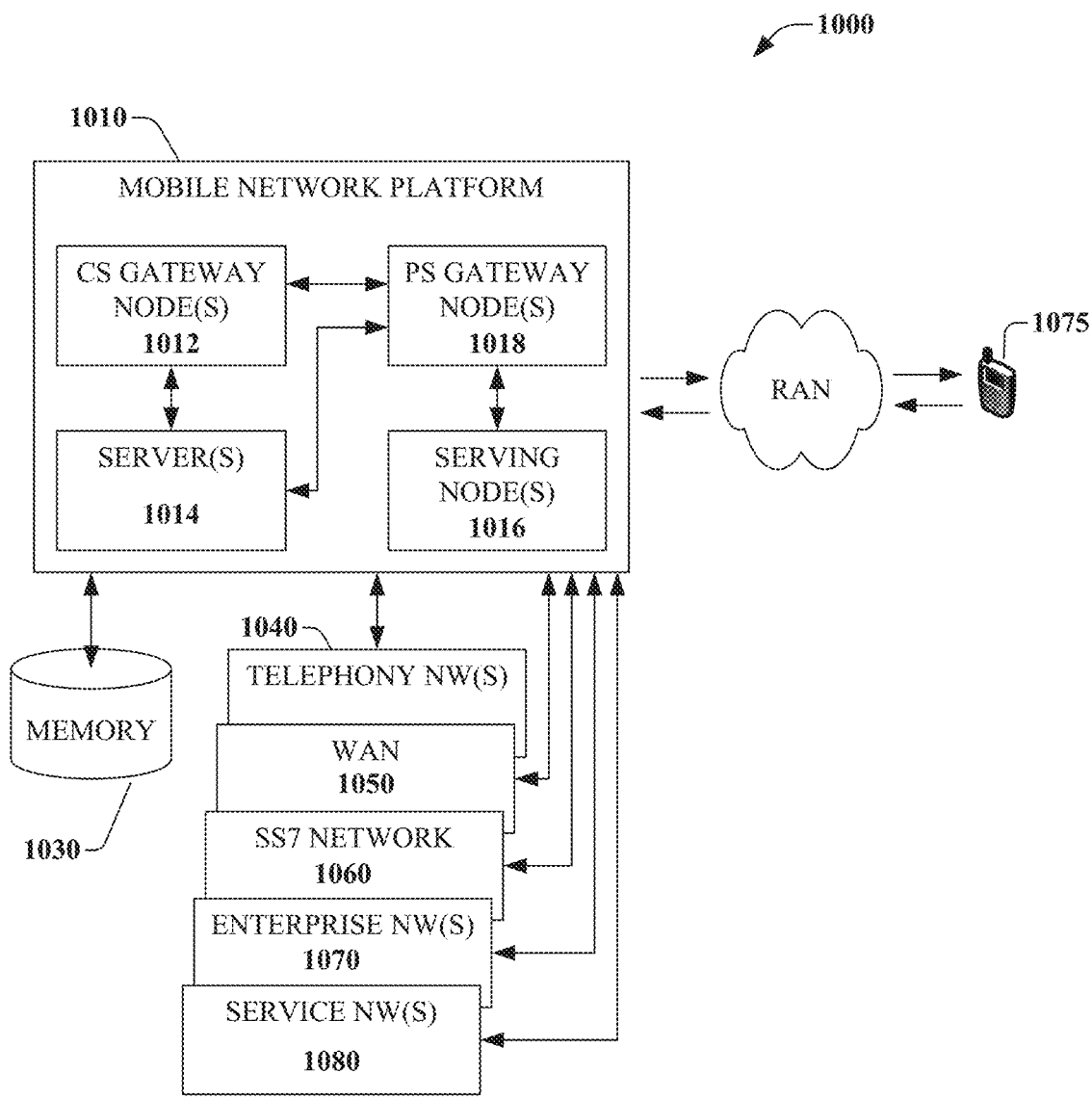
FIG. 10 is a block diagram of an example, non-limiting embodiment of a mobile network platform in accordance with various aspects described herein.

FIG. 10 presents an example embodiment 1000 of a mobile network platform 1010 that can implement and exploit one or more aspects of the disclosed subject matter described herein. Generally, wireless network platform 1010 can comprise components, e.g., nodes, gateways, interfaces, servers, or disparate platforms, that facilitate both packet-switched (PS) (e.g., internet protocol (IP), frame relay, asynchronous transfer mode (ATM)) and circuit-switched (CS) traffic (e.g., voice and data), as well as control generation for networked wireless telecommunication. As a non-limiting example, wireless network platform 1010 can be included in telecommunications carrier networks, and can be considered carrier-side components as discussed elsewhere herein. Mobile network platform 1010 comprises CS gateway node(s) 1012 which can interface CS traffic received from legacy networks like telephony network(s) 1040 (e.g., public switched telephone network (PSTN), or public land mobile network (PLMN)) or a signaling system #7 (SS7) network 1070. Circuit switched gateway node(s) 1012 can authorize and authenticate traffic (e.g., voice) arising from such networks. Additionally, CS gateway node(s) 1012 can access mobility, or roaming, data generated through SS7 network 1070; for instance, mobility data stored in a visited location register (VLR), which can reside in memory 1030. Moreover, CS gateway node(s) 1012 interfaces CS-based traffic and signaling and PS gateway node(s) 1018. As an example, in a 3GPP UMTS network, CS gateway node(s) 1012 can be realized at least in part in gateway GPRS support node(s) (GGSN). It should be appreciated that functionality and specific operation of CS gateway node(s) 1012, PS gateway node(s) 1018, and serving node(s) 1016, is provided and dictated by radio technology(ies) utilized by mobile network platform 1010 for telecommunication. Mobile network platform 1010 can also comprise the MMEs, HSS/PCRFs, SGWs, and PGWs disclosed herein.

In addition to receiving and processing CS-switched traffic and signaling, PS gateway node(s) 1018 can authorize and authenticate PS-based data sessions with served mobile devices. Data sessions can comprise traffic, or content(s), exchanged with networks external to the wireless network platform 1010, like wide area network(s) (WANs) 1050, enterprise network(s) 1070, and service network(s) 1080, which can be embodied in local area network(s) (LANs), can also be interfaced with mobile network platform 1010 through PS gateway node(s) 1018. It is to be noted that WANs 1050 and enterprise network(s) 1060 can embody, at least in part, a service network(s) like IP multimedia subsystem (IMS). Based on radio technology layer(s) available in technology resource(s) 1017, packet-switched gateway node(s) 1018 can generate packet data protocol contexts when a data session is established; other data structures that facilitate routing of packetized data also can be generated. To that end, in an aspect, PS gateway node(s) 1018 can comprise a tunnel interface (e.g., tunnel termination gateway (TTG) in 3GPP UMTS network(s) (not shown)) which can facilitate packetized communication with disparate wireless network(s), such as Wi-Fi networks.

In embodiment 1000, wireless network platform 1010 also comprises serving node(s) 1016 that, based upon available radio technology layer(s) within technology resource(s) 1017, convey the various packetized flows of data streams received through PS gateway node(s) 1018. It is to be noted that for technology resource(s) 1017 that rely primarily on CS communication, server node(s) can deliver traffic without reliance on PS gateway node(s) 1018; for example, server node(s) can embody at least in part a mobile switching center. As an example, in a 3GPP UMTS network, serving node(s) 1016 can be embodied in serving GPRS support node(s) (SGSN).

For radio technologies that exploit packetized communication, server(s) 1014 in wireless network platform 1010 can execute numerous applications that can generate multiple disparate packetized data streams or flows, and manage (e.g., schedule, queue, format . . . ) such flows. Such application(s) can comprise add-on features to standard services (for example, provisioning, billing, customer support . . . ) provided by wireless network platform 1010. Data streams (e.g., content(s) that are part of a voice call or data session) can be conveyed to PS gateway node(s) 1018 for authorization/authentication and initiation of a data session, and to serving node(s) 1016 for communication thereafter. In addition to application server, server(s) 1014 can comprise utility server(s), a utility server can comprise a provisioning server, an operations and maintenance server, a security server that can implement at least in part a certificate authority and firewalls as well as other security mechanisms, and the like. In an aspect, security server(s) secure communication served through wireless network platform 1010 to ensure network's operation and data integrity in addition to authorization and authentication procedures that CS gateway node(s) 1012 and PS gateway node(s) 1018 can enact. Moreover, provisioning server(s) can provision services from external network(s) like networks operated by a disparate service provider; for instance, WAN 1050 or Global Positioning System (GPS) network(s) (not shown). Provisioning server(s) can also provision coverage through networks associated to wireless network platform 1010 (e.g., deployed and operated by the same service provider), such as femto-cell network(s) (not shown) that enhance wireless service coverage within indoor confined spaces and offload RAN resources in order to enhance subscriber service experience within a home or business environment by way of UE 1075.

It is to be noted that server(s) 1014 can comprise one or more processors configured to confer at least in part the functionality of macro network platform 1010. To that end, the one or more processor can execute code instructions stored in memory 1030, for example. It is should be appreciated that server(s) 1014 can comprise a content manager 1015, which operates in substantially the same manner as described hereinbefore.

In example embodiment 1000, memory 1030 can store information related to operation of wireless network platform 1010. Other operational information can comprise provisioning information of mobile devices served through wireless platform network 1010, subscriber databases; application intelligence, pricing schemes, e.g., promotional rates, flat-rate programs, couponing campaigns; technical specification(s) consistent with telecommunication protocols for operation of disparate radio, or wireless, technology layers; and so forth. Memory 1030 can also store information from at least one of telephony network(s) 1040, WAN 1050, enterprise network(s) 1060, or SS7 network 1070. In an aspect, memory 1030 can be, for example, accessed as part of a data store component or as a remotely connected memory store.

In order to provide a context for the various aspects of the disclosed subject matter, FIGS. 9 and 10, and the following discussion, are intended to provide a brief, general description of a suitable environment in which the various aspects of the disclosed subject matter can be implemented. While the subject matter has been described above in the general context of computer-executable instructions of a computer program that runs on a computer and/or computers, those skilled in the art will recognize that the disclosed subject matter also can be implemented in combination with other program modules. Generally, program modules comprise routines, programs, components, data structures, etc. that perform particular tasks and/or implement particular abstract data types.

In the subject specification, terms such as "store," "storage," "data store," data storage," "database," and substantially any other information storage component relevant to operation and functionality of a component, refer to "memory components," or entities embodied in a "memory" or components comprising the memory. It will be appreciated that the memory components described herein can be either volatile memory or nonvolatile memory, or can comprise both volatile and nonvolatile memory, by way of illustration, and not limitation, volatile memory (see below), non-volatile memory (see below), disk storage (see below), and memory storage (see below). Further, nonvolatile memory can be included in read only memory (ROM), programmable ROM (PROM), electrically programmable ROM (EPROM), electrically erasable ROM (EEPROM), or flash memory. Volatile memory can comprise random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

Moreover, it will be noted that the disclosed subject matter can be practiced with other computer system configurations, comprising single-processor or multiprocessor computer systems, mini-computing devices, mainframe computers, as well as personal computers, hand-held computing devices (e.g., PDA, phone, watch, tablet computers, netbook computers, . . . ), microprocessor-based or programmable consumer or industrial electronics, field programmable gate array, graphics processor, or software defined radio reconfigurable processor and the like. The illustrated aspects can also be practiced in distributed computing environments where tasks are performed by remote processing devices that are linked through a communications network; however, some if not all aspects of the subject disclosure can be practiced on stand-alone computers. In a distributed computing environment, program modules can be located in both local and remote memory storage devices.

The embodiments described herein can employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out various embodiments thereof. Moreover, the classifier can be employed to determine a ranking or priority of the each cell site of the acquired network. A classifier is a function that maps an input attribute vector, $x=(x1, x2, x3, x4, \ldots, xn)$, to a confidence that the input belongs to a class, that is, $f(x)=$confidence (class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches comprise, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing UE behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a predetermined criteria which of the acquired cell sites will benefit a maximum number of subscribers and/or which of the acquired cell sites will add minimum value to the existing communication network coverage, etc.

As used in this application, in some embodiments, the terms "component," "system" and the like are intended to refer to, or include, a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, computer-executable instructions, a program, and/or a computer. By way of illustration and not limitation, both an application running on a server and the server can be a component. One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software or firmware that confers at least in part the functionality of the electronic components. While various components have been illustrated as separate components, it will be appreciated that multiple components can be implemented as a single component, or a single component can be implemented as multiple components, without departing from example embodiments.

Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer program accessible from any computer-readable device or computer-readable storage/communications media. For example, computer readable storage media can comprise, but are not limited to, magnetic storage devices (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Moreover, terms such as "user equipment," "mobile station," "mobile," subscriber station," "access terminal," "terminal," "handset," "mobile device" (and/or terms representing similar terminology) can refer to a wireless device utilized by a subscriber or user of a wireless communication service to receive or convey data, control, voice, video, sound, gaming or substantially any data-stream or signaling-stream. The foregoing terms are utilized interchangeably herein and with reference to the related drawings.

Furthermore, the terms "user," "subscriber," "customer," "consumer" and the like are employed interchangeably throughout, unless context warrants particular distinctions among the terms. It should be appreciated that such terms can refer to human entities or automated components supported through artificial intelligence (e.g., a capacity to make inference based, at least, on complex mathematical formalisms), which can provide simulated vision, sound recognition and so forth.

As employed herein, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of user equipment. A processor can also be implemented as a combination of computing processing units.

What has been described above includes mere examples of various embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system, comprising:
   a processor; and
   a memory that stores executable instructions that, when executed by the processor, facilitate performance of operations, comprising:
      determining that a first data stream comprises protected information based on an indication of a type of application associated with the first data stream, the determining further being a function of a location of a first device associated with the first data stream, a time that the first data stream is received, and a user profile active on the first device, wherein the protected information is electronic personal healthcare information;
      in response to determining that the first data stream comprises the protected information, encrypting the first data stream resulting in an encrypted data stream; and
      transmitting, via a network device of a mobile network, the encrypted data stream and a second data stream that does not comprise the electronic personal healthcare information, wherein the encrypted data stream is transmitted via a first communication channel, and the second data stream is transmitted via a second communication channel segregated from the first communication channel.

2. The system of claim 1, wherein the operations further comprise:
   adding metadata to the encrypted data stream indicating that the encrypted data stream comprises the protected information resulting in a modified first data stream.

3. The system of claim 2, wherein the metadata comprises information relating to the application and a profile preference related to the application.

4. The system of claim 2, wherein the operations further comprise:
   performing a network function related to a quality of service and a quality of experience on the encrypted data stream based on the metadata.

5. The system of claim 1, wherein the first data stream and the second data stream are associated with different applications on the first device, wherein a first application associated with the first data stream generates protected information and a second application associated with the second data stream does not generate the protected information.

6. The system of claim 1, wherein the operations further comprise:
   transmitting the encrypted data stream to a second device.

7. The system of claim 6, wherein the operations further comprise:
   facilitating an encrypted connection between a first secure application of the first device and a second secure application of the second device.

8. The system of claim 1, wherein the operations further comprise:
   transmitting the encrypted data stream to a remote patient monitoring database.

9. The system of claim 1, wherein the operations further comprise:
   authenticating the first device based on authentication triplets and a virtual subscriber identity module card.

10. The system of claim 1, wherein the user profile is associated with a policy for management of electronic personal healthcare information.

11. A method, comprising:
    determining, by a device comprising a processor, that a first data stream from a user equipment device comprises private information based on a determination of an application on the user equipment device associated with the first data stream, a location of the user equipment device, a time that the first data stream was received, and a policy associated with a user profile active on the user equipment associated with the first data stream, wherein the application is associated with electronic personal healthcare information;
    in response to determining that the first data stream comprises the private information, encrypting, by the device, the first data stream resulting in an encrypted data stream; and
    transmitting, by the device, the encrypted data stream and a second data stream that does not comprise the electronic personal healthcare information, wherein the encrypted data stream is transmitted via a first communication channel, and the second data stream is transmitted via a second communication channel segregated from the first communication channel.

12. The method of claim 11, further comprising:
    generating, by the device, metadata that indicates that the encrypted data stream comprises the private information; and
    attaching, by the device, the metadata to the encrypted data stream resulting in an updated first data stream.

13. The method of claim 12, wherein the metadata comprises information relating to profile preference information associated with the application.

14. The method of claim 11, wherein the user equipment device is a first user equipment device, and wherein the transmitting further comprises transmitting the updated first data stream to a second user equipment device.

15. The method of claim 14, further comprising:
    enabling, by the device, an encrypted connection between respective secure applications of the first user equipment device and the second user equipment device.

16. The method of claim 11, wherein the transmitting further comprises transmitting the updated first data stream to a remote monitoring database.

17. The method of claim 11, wherein the first data stream and the second data stream are associated with different applications on the user equipment device.

18. A non-transitory machine-readable storage medium, comprising executable instructions that, when executed by a processor, facilitate performance of operations, comprising:
    based on an application on the user equipment associated with the data stream, a location of the user equipment, a time that the data stream is received from the user equipment, and a policy associated with a user profile active on the user equipment, determining that a data stream associated with a user equipment device comprises private information representative of electronic personal healthcare information; encrypting the data stream resulting in an encrypted data stream; based on the policy associated with the user profile, performing a network function related to a quality of service and a quality of experience on the encrypted data stream; and
    transmitting the encrypted data stream and a second data stream that does not comprise any electronic personal healthcare information, wherein the encrypted data stream is transmitted via a first communication channel, and the second data stream is transmitted via a second communication channel segregated from the first communication channel.

19. The non-transitory machine-readable storage medium of claim 18, wherein the application is a first application, and wherein the second data stream originates from a second application that does not generate any electronic personal healthcare information.

20. The non-transitory machine-readable storage medium of claim 18, wherein the encrypted data stream comprises metadata indicating information relating to profile preference information associated with the application.

\* \* \* \* \*